United States Patent [19]

Gupte

[11] Patent Number: 4,609,674
[45] Date of Patent: Sep. 2, 1986

[54] STABILIZED CLEAR BENZOYL PEROXIDE COMPOSITIONS

[75] Inventor: Anil J. Gupte, Seymour, Conn.

[73] Assignee: Richardson-Vicks Inc., Wilton, Conn.

[21] Appl. No.: 619,386

[22] Filed: Jun. 11, 1984

[51] Int. Cl.$^4$ .................. A61K 31/075; A61K 31/225
[52] U.S. Cl. ..................................... 514/547; 514/714; 514/859
[58] Field of Search ............... 424/338; 514/547, 714, 514/859

[56] References Cited

U.S. PATENT DOCUMENTS

| | | | |
|---|---|---|---|
| 3,535,422 | 10/1970 | Cox et al. | 424/164 |
| 4,172,149 | 10/1979 | Pinto et al. | 424/312 |
| 4,189,501 | 2/1980 | Fulton | 424/338 |
| 4,355,028 | 10/1982 | Kligman et al. | |
| 4,372,296 | 2/1983 | Fahim | 128/24 A |

Primary Examiner—Leonard Schenkman
Attorney, Agent, or Firm—George W. Rauchfuss, Jr.; Salvatore R. Conte

[57] ABSTRACT

A stabilized clear benzoyl peroxide composition is provided comprising from about 0.1 to about 3.8% by weight anhydrous benzoyl peroxide in $C_6$–$C_{10}$ triglycerides.

12 Claims, No Drawings

STABILIZED CLEAR BENZOYL PEROXIDE COMPOSITIONS

FIELD OF THE INVENTION

This invention relates to stabilized clear benzoyl peroxide compositions which are useful in the treatment of acne. Decomposition of the benzoyl peroxide during storage is prevented.

BACKGROUND OF THE INVENTION

The topical application of benzoyl peroxide has been found to be effective in the treatment of acne vulgaris, as disclosed for example in U.S. Pat. No. 3,535,422, issued Oct. 20, 1970 to Richard M. Cox and Leonard R. Ciafo and assigned to Steifel Laboratories, Inc. Benzoyl peroxide compositions have become the leading anti-acne compositions due to the antimicrobial effect of benzoyl peroxide on Propionobacterium Acne, the main anaerobic acne causing bacteria. Generally the benzoyl peroxide is topically applied as a suspension containing from about 2.5 to about 10% w/w benzoyl peroxide.

However, the effectiveness of the benzoyl peroxide in the treatment of acne has proven to be a function of the stability of the benzoyl peroxide and the benzoyl peroxide composition applied to the affected region. Benzoyl peroxide is, however, very unstable in solution and degrades rapidly to inactive benzoic acid. Prior benzoyl peroxide compositions have decomposed rapidly during storage and therefore do not have a reasonable shelf life. Yet, decomposition of benzoyl peroxide when in contact with skin is highly desirable since it is the oxidizing effect of the free radicals produced on decomposition that provides the desired anti-acne effect.

It is therefore highly desirable to obtain a benzoyl peroxide composition which is stable during storage and yet decomposes readily on contact with skin. Moreover, it would be even more desirable that such a benzoyl peroxide composition be clear since benzoyl peroxide itself is a colorless, odorless crystalline solid.

SUMMARY OF THE INVENTION

It has been discovered that stable, clear compositions of benzoyl peroxide can be obtained by the use of $C_6$ to $C_{10}$ triglycerides in which benzoyl peroxide is dissolved.

DETAILS OF THE INVENTION

Compositions of the invention comprise stable, clear, anhydrous compositions of about 0.1 to about 3.8% w/w of benzoyl peroxide in q.s. to 100% of short chain triclycerides of the general formula

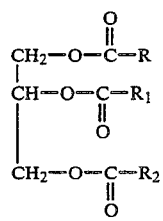

wherein R, $R_1$ and $R_2$ are straight or branched chain saturated, aliphatic hydrocarbon radicals containing from 6 to 10 carbon atoms. R, $R_1$ and $R_2$ may be the same or different aliphatic hydrocarbon radical. The acyl portion of the radical is generaly derived from a fatty acid such as caproic, enanthylic, caprylic, pelargonic or capric acid. In accordance with this invention, single triglycerides or mixtures of triglycerides may be employed such as tricaproin, tricaprylin, tricaprin or mixtures thereof.

The compositions of this invention can, if desired, also have a gelling agent present, generally in an amount up to about 8% w/w. A preferred gelling agent is silica. Other optional components may also be present, such as, for example, a minor amount of up to about 2% w/w of a lubricant. As an example of a lubricant, there can be mentioned low molecular weight silicone oil, such as, for example, cyclomethicone and the like.

A typical composition of this invention comprises the following benzoyl peroxide gel:

| Component | Amount % w/w |
|---|---|
| Benzoyl peroxide, anhydrous | 0.1-3.8% |
| Gelling agent | up to 8.0% |
| Lubricant | up to 2.0% |
| Triglyceride | q.s. to 100.0% |

A preferred composition of this invention comprises a benzoyl peroxide gel of the following composition:

| Component | Amount % w/w |
|---|---|
| Benzoyl peroxide, anhydrous | 2.5% |
| $C_8$—$C_{10}$ triglyceride 60/40 mixture | 87.5% |
| Silica | 8.0% |
| Cyclomethicone (Dow Corning 344 Fluid) | 2.0% |

The benzoyl peroxide clear solution is first prepared in triglyceride and then other optional components such as gelling agents, lubricants and the like are added to produce the clear gel product.

The preferred composition is clear and stable with 91% benzoyl peroxide remaining after six months' storage at room temperature. Moreover, said composition was found to be effective in reducing the P. Acne causing skin microflora by 1.5 to 2.0 logarithims when the composition was tested in a ten (10) day in-vivo antimicrobial study performed on three volunteers in which the composition was applied twice a day to the face area in half face fashion. Skin microflora was obtained on days 2, 3, 5 and 10 and after appropriate incubation under anaerobic conditions, the skin microflora was measured. The reduction in bacteria was determined by comparing the number of microorganisms between the treated and untreated sides of the faces.

Acne is treated in patients by the topical application to the patient of an anti-acne effective amount of the clear stable compositions of this invention.

I claim:

1. A clear stable anhydrous benzoyl peroxide anti-acne composition comprising from about 0.1 to about 3.8% w/w anhydrous benzoyl peroxide in a $C_6$ to $C_{10}$ triglyceride.

2. A composition of claim 1 wherein the benzoyl peroxide is present in the composition in an amount of about 2.5% w/w.

3. A composition of claim 1 containing a gelling agent.

4. A composition of claim 2 containing a gelling agent.

5. An anti-acne composition of claim 3 comprising:

| | |
|---|---|
| about 0.1 to about 3.8% w/w | benzoyl peroxide, anhydrous |
| up to about 8.0% w/w | gelling agent |
| up to about 2.0% w/w | lubricant |
| q.s. to 100.0% w/w | triglyceride |

6. An anti-acne composition of claim 3 comprising:

| | |
|---|---|
| about 2.5% w/w | benzoyl peroxide, anhydrous |
| about 87.5% w/w | $C_8$—$C_{10}$ triglyceride mixture |
| about 8.0% w/w | silica |
| about 2.0% w/w | cyclomethicone |

7. A method for the treatment of acne in a patent in need thereof comprising the topical application of an anti-acne effective amount of the composition of claim 1 to said patent.

8. A method for the treatment of acne in a patent in need thereof comprising the topical application of an anti-acne effective amount of the composition of claim 2 to said patent.

9. A method for the treatment of acne in a patent in need thereof comprising the topical application of an anti-acne effective amount of the composition of claim 3 to said patent.

10. A method for the treatment of acne in a patent in need thereof comprising the topical application of an anti-acne effective amount of the composition of claim 4 to said patent.

11. A method for the treatment of acne in a patent in need thereof comprising the topical application of an anti-acne effective amount of the composition of claim 5 to said patent.

12. A method for the treatment of acne in a patent in need thereof comprising the topical application of an anti-acne effective amount of the composition of claim 6 to said patent.

* * * * *